United States Patent [19]

Carlson

[11] 4,033,959

[45] July 5, 1977

[54] PROCESS FOR PREPARING CHLOROISOCYANURATE COMPLEX COMPOUNDS

[75] Inventor: Ronald H. Carlson, Willingboro, N.J.

[73] Assignee: FMC Corporation, Philadelphia, Pa.

[22] Filed: July 19, 1976

[21] Appl. No.: 706,274

[52] U.S. Cl. .................................. 260/248 C
[51] Int. Cl.$^2$ .................................. C07D 251/36
[58] Field of Search ........................... 260/248 C

[56] References Cited

UNITED STATES PATENTS

| | | | |
|---|---|---|---|
| 3,150,132 | 9/1964 | Symes | 260/248 |
| 3,256,199 | 6/1966 | Symes | 252/99 |
| 3,272,813 | 9/1966 | Symes | 260/248 |
| 3,275,630 | 9/1966 | Symes | 260/248 |
| 3,325,411 | 6/1967 | Stepanek | 252/99 |
| 3,501,468 | 3/1970 | Moore et al. | 260/248 |
| 3,538,005 | 11/1970 | Weinstein et al. | 252/99 |
| 3,888,856 | 6/1975 | Wojtowicz | 260/248 |
| 3,894,017 | 7/1975 | Wojtowicz et al. | 260/248 |
| 3,898,223 | 8/1975 | Wojtowicz | 260/248 |

*Primary Examiner*—John M. Ford
*Attorney, Agent, or Firm*—Christine M. Miles

[57] ABSTRACT

Processes are described for the preparation of certain potassium-containing chloroisocyanurate complex compounds, namely, hydrated and non-hydrated [(mono-trichloro,) tetra(monopotassium dichloro,)] penta-isocyanurate, which are useful as bleaching, sterilizing, oxidizing and disinfecting agents. These processes involve reacting in a substantially dry state, potassium dichloroisocyanurate monohydrate and a dichloroisocyanuric acid compound in amounts such that the molar ratio of the potassium dichloroisocyanurate monohydrate to said acid compound is in the range of 1:1 to 3:1.

8 Claims, No Drawings

PROCESS FOR PREPARING CHLOROISOCYANURATE COMPLEX COMPOUNDS

This application is related to a patent application entitled Novel Chloroisocyanurate Compounds, filed concurrently with this application, in the name of Sidney Berkowitz, Ser. No. 706,275.

This invention relates to processes for the preparation of hydrated and non-hydrated [(mono-trichloro,) tetra-(monopotassium dichloro,)] penta-isocyanurate, which involve reacting in a substantially dry state, potassium dichloroisocyanurate monohydrate and a dichloroisocyanuric acid compound.

Chlorinated isocyanurates such as dichloroisocyanuric acid, alkali metal salts thereof, hydrates of said alkali metal salts, trichloroisocyanuric acid, and the potassium-containing chloroisocyanurate complex compounds [(monotrichloro,) tetra-(monopotassium dichloro,)] penta-isocyanurate and (mono-trichloro,) (monopotassium dichloro,) diisocyanurate, are well known as sources of available chlorine, and are useful, for example, in bleaching, sterilizing, oxidizing and disinfecting operations.

[(Mono-trichloro,) tetra-(monopotassium dichloro,)] penta-isocyanurate and (mono-trichloro,) (monopotassium dichloro,) di-isocyanurate, referred to as Compound I and Compound II respectively, and processes for their preparation are disclosed in U.S. Pat. Nos. 3,150,132, 3,272,813 (division of 3,150,132), 3,275,630 (continuation-in-part of 3,150,132) and 3,501,468. These patents disclose one process for the exclusive preparation of Compound I, and processes for the preparation of either Compounds I or II, singly or mixtures thereof. All of the disclosed processes involve liquid state reactions in aqueous solvent systems which require careful control of pH and reactant ratios.

Specifically, U.S. Pat. No. 3,275,630 discloses the exclusive preparation of Compound I by reacting an aqueous solution of monopotassium dichloroisocyanurate with an acid incapable of undergoing an oxidation-reduction reaction with the chloroisocyanurate starting material and reaction product. The acid reactant must be added to the reaction zone in an amount and at a rate sufficient to maintain a pH within the range of 4.6–5.0.

U.S. Pat. No. 3,150,132 discloses a process for the preparation of either Compounds I or II singly or mixtures thereof, by reacting chlorine and an aqueous solution of tripotassium cyanurate in a reaction zone containing a heel of an aqueous slurry of Compounds I or Ii or a mixture thereof, the particular compound or mixture produced depends upon the pH of the reaction system which is adjusted by controlling the rate of introducing the chlorine and tripotassium cyanurate into the reaction zone. U.S. Pat. No. 3,501,468 discloses a variation of this process which involves substitution of the tripotassium cyanurate reactant with a specifically defined sodium-potassium cyanurate compound.

Lastly, U.S. Pat. Nos. 3,150,132 and 3,272,813 disclose a process for the preparation of either Compounds I or II singly or mixtures thereof by reacting monopotassium dichloroisocyanurate and trichloroisocyanuric acid in an inert liquid. The particular compound or mixture produced depends upon the pH of the inert liquid and the ratio of reactants which are accordingly adjusted and controlled.

There are serious disadvantages to the above described prior art processes. Firstly, the careful control of pH and reactant ratios required is difficult to achieve, especially where large scale commercial production is involved. Secondly, chlorinated isocyanurates, particularly trichloroisocyanuric acid, decompose in aqueous solvent systems to produce nitrogen trichloride, an extremely unstable compound which is explosive upon reaction with an organic compound, or at a temperature higher than 60° C. Decomposition of chlorinated cyanurates to form nitrogen trichloride is known to be pH dependent. Specifically, the decomposition of trichloroisocyanurate in aqueous solvent systems, to form nitrogen trichloride, peaks at a pH of about 5, which is near the midpoint of the pH range for formation of Compound I by the processes of the prior art (see U.S. Pat. No. 3,534,033). Consequently, there is a need for providing a process for production of potassium-containing chloroisocyanurate complex compounds which has the practical advantage of not requiring careful pH control and the safety advantage of not producing dangerous levels of nitrogen trichloride.

It has been unexpectedly discovered that hydrated [(mono-trichloro,) tetra-(monopotassium dichloro,)] pentaisocyanurate (Compound III) can be prepared by bringing together and reacting in a substantially dry state potassium dichloroisocyanurate monohydrate and dichloroisocyanuric acid monohydrate, in amounts such that the molar ratio of the potassium dichloroisocyanurate monohydrate to said acid is in the range of 1:1 to 3:1, and further, that this hydrated reaction product can be dried, or compacted under pressure, to produce non-hydrated [(mono-trichloro,) tetra-(monopotassium dichloro,)] penta-isocyanurate. Further, it has been discoverd that non-hydrated [(mono-trichloro,) tetra-(monopotassium dichloro,)] penta-isocyanurate can be prepared by bringing together under pressure and reacting in a substantially dry state, potassium dichloroisocyanurate monohydrate and non-hydrated dichloroisocyanuric acid, in amounts such that the molar ratio of said monohydrate to said acid is in the range of 1:1 to 3:1.

In carrying out the above reactions, cyanuric acid and other impurities may be formed and be present as minor components in the reaction products. The total amount of minor components present in the reaction products, based upon X-ray diffraction analyses, is less than 20% by weight. Other minor components which may be present include, for example, dichloroisocyanuric acid, potassium dichloroisocyanurate, and (mono-trichloro) (monopotassium dichloro) diisocyanurate. These reaction products are suitable as such for use, in for example, bleaching and disinfecting operations, however they may be purified if desired.

It is an object of the present invention to provide processes for the preparation of Compounds I and III.

Additional objects and advantages of the present invention will become apparent from the following description and the appended claims.

It will be understood throughout the specification and claims that various chemical terms are used interchangeably. For example, the terms "cyanurate" and "isocyanurate" refer to the same compounds but connotate different tautomeric forms thereof.

The potassium dichloroisocyanurate monohydrate reactant used in the process of this invention, may be prepared by dissolving commercially available anhydrous potassium dichloroisocyanurate in water, filtering the solution to remove impurities, and cooling the filtrate to about 3° C. in a brine bath. The monohydrate crystals formed thereby are then filtered, washed with a suitable solvent, as for example, acetone, and dried. The dichloroisocyanuric acid monohydrate reactant may be prepared by slurrying non-hydrated dichloroisocyanuric acid in water, and filtering the slurry to obtain a wet cake, which is washed with water and dried by, for example, room temperature air and/or vacuum drying. The non-hydrated dichloroisocyanuric acid used in the process of this invention and in the preparation of dichloroisocyanuric acid monohydrate may be prepared by any of the processes described in U.S. Pat. Nos. 2,969,360, 3,120,552, 3,453,274, 3,668,204, 3,757,018 and 3,712,891, which disclosures are incorporated by reference in this application for patent.

Compounds I and III may be prepared from a substantially dry state reaction of potassium dichloroisocyanurate monohydrate and dichloroisocyanuric acid monohydrate wherein the molar ratio of the potassium dichloroisocyanurate monohydrate to said acid is in the range of 1:1 to 3:1. When it is desired to prepare Compound III, the potassium dichloroisocyanurate monohydrate and dichloroisocyanuric acid monohydrate are brought together and reacted by blending in, for example, a tumble-type blender. The X-ray diffraction pattern of the blended product showed formation of a hydrated complex compound, and is similar to that of [(mono-trichloro,) tetra-(monopotassium dichloro,)] penta-isocyanurate tetrahydrate. From this information, it is concluded that this hydrated product is a tetrahydrate. Compound III, will lose water of hydration on standing when exposed to air. Such loss, however, can be prevented by the methods disclosed in the aforementioned concurrently filed patent application, whose disclosure is incorporated by reference herein, which include storage in sealed containers or microencapsulation of the compound with materials such as modified dextrins, starches, and polyvinyl alcohols.

When it is desired to prepare Compound I the aforementioned blended product may be dehydrated by either compacting said product under pressure or by conventional drying means as for example, air, vacuum, or fluidized bed drying. Compaction of the blended product at a pressure within the range of from about 1,000 psig to about 20,000 psig is sufficient for the preparation of Compound I. The X-ray diffraction patterns of both a compacted product and a blended product air dried at room temperature for about three days, are identical and compare well with that of commercialy available Compound I.

It has also been found that Compound I may be prepared by bringing together and reacting in a substantially dry state potassium dichloroisocyanurate monohydrate and non-hydrated dichloroisocyanuric acid, by blending said reactants in amounts such that the molar ratio of the potassium dichloroisocyanurate monohydrate to said acid is in the range 1:1 to 3:1, and by compacting the blended product under a pressure of from about 1,000 psig to about 20,000 psig. The X-ray diffraction pattern of this compacted product compares well with that of commercially available Compound I. X-ray diffraction analysis further shows that this reaction does not occur upon simple blending of the reactants.

A further understanding of the novel processes of the present invention will be obtained from the following examples which are intended to illustrate the invention, but not to limit the scope thereof. Parts and percentages are by weight unless otherwise specified.

EXAMPLE I

Preparation of hydrated [(mono-trichloro,) tetra-(monopotassium dichloro,)] penta-isocyanurate,

Compound III

The potassium dichloroisocyanurate monohydrate used in the reaction of this example waas prepared by dissolving 440 grams of commercially available potassium dichloroisocyanurate in 4,400 ml of water at a temperature within the range of 37 to 40° C. The solution was filtered to remove a small amount of insolubles, and the filtrate cooled to 3° C. in a brine bath. Well defined crystals of potassium dichloroisocyanurate monohydrate began forming at 12° C. The crystals were filtered, washed with 700 ml of acetone and air dried overnight. The dichloroisocyanuric acid monohydrate reactant was formed by slurring 194 grams of dichloroisocyanuric acid, prepared according to the process described in U.S. Pat. No. 2,969,360 and 822 milliliters of distilled water for 15 minutes at room temperature. The slurry was filtered to obtain the dichloroisocyanuric acid monohydrate in the form of a wet cake, which was washed four times with 105 milliliter portions of ice cold distilled water, hand pressed to remove excess water, and subjected to air and vacuum drying at room temperature.

Ten and 16 hundredths grams (0.04 moles) of potassium dichloroisocyanurate monohydrate and 4.32 grams (0.02moles) of dichloroisocyanuric acid monohydrate were charged into a tumble-type blender and blended for ten minutes. The blended product was subjected to X-ray diffraction analysis which showed formation of a hydrated complex compound. This X-ray diffraction pattern compared well with that of commercially available Compound I except for the presence of hydrate water peaks 2 $\theta$ values of 13.8 and 27.7. The pattern, including the hydrate water peaks, compares with that of [(mono-trichloro,) tetra(-monopotassium dichloro,)] penta-isocyanurate tetrahydrate. It is therefore believed this hydrated product is said tetrahydrate.

EXAMPLE II

Preparation of [(mono-trichloro) tetra-(monopotassium dichloro,)] penta-isocyanurate,

Compound I

Run A - Process of the Invention

About 10 grams of blended product prepared by the process of Example I were compacted in a hydraulic press at a pressure of 15,000 psig. Pressure was maintained for two minutes. The compacted product was ground into a powder and subjected to X-ray diffraction analysis which showed the formation of a non-hydrated complex compound. The X-ray diffraction pattern of this compacted product compared well with that of commercially available Compound I.

Run B — Comparative Example

An attempt was made to prepare Compound I, by blending and then compacting under pressure a commercially available sample of anhydrous potassium dichloroisocyanurate and non-hydrated dichloroisocyanuric acid prepared according to the process described in U.S. Pat. No. 2,969,360.

In this test, 9.44 grams (0.04 moles) of potassium dichloroisocyanurate and 3.96 grams (0.02 moles of dichloroisocyanuric acid were charged into a tumble-type blender and blended for ten minutes. About 10 grams of the blended product were compacted in a hydraulic press at a pressure of 15,000 psig. Pressure was maintained for two minutes. The compacted product was ground into a powder and subjected to X-ray diffraction analysis which showed only a physical mixture of the reactants.

EXAMPLE III

Preparation of [(mono-trichloro) tetra-(monopotassium dichloro,)] penta-isocyanurate, Compound I About 10 grams of blended product prepared by the process of Example I were placed in an uncovered Petri dish, allowed to stand exposed to air at a temperature of about 25° C for 3 days, and then subjected to X-ray diffraction analysis. The X-ray diffraction pattern of this material compared well with that of commercially available Compound I.

EXAMPLE IV

Preparation of [(mono-trichloro,) tetra-(monopotassium dichloro,)] penta-isocyanurate, Compound I 10 and 16 hundredths grams (0.04 moles) of potassium dichloroisocyanurate monohydrate prepared according to the procedure described in Example I, and 3.96 grams (0.02 moles) of non-hydrated dichloroisocyanuric acid, prepared according to the process described in U.S. Pat. No. 2,969,360, were charged into a tumble-type blender and blended for 10 minutes. About 10 grams of the blended product were compacted in a hydraulic press at a pressure of 15,000 psig. Pressure was maintained for 2 minutes. The compacted product was ground into a powder and subjected to X-ray diffraction analysis which showed the formation of a complex compound. The X-ray diffraction pattern of this compacted product compared well with that of commercially available Compound I.

What is claimed is:

1. A process for preparing hydrated {(mono-trichloro,) tetra-(monopotassium dichloro,)} penta-isocyanurate, which comprises bringing together and reacting in a substantially dry state potassium dichloroisocyanurate monohydrate and dichloroisocyanuric acid monohydrate in amounts such that the molar ratio of said monohydrate to said acid is in the range of 1:1 to 3:1.

2. Process of claim 1 wherein the potassium dichloroisocyanurate monohydrate and dichloroisocyanuric acid monohydrate are brought together and reacted by blending.

3. Process of claim 1 wherein the hydrated reaction product is compacted under a pressure of from about 1,000 psig to about 20,000 psig to produce non-hydrated {(monotrichloro,) tetra-(monopotassium dichloro,)} penta-isocyanurate.

4. Process of claim 1 wherein the hydrated reaction product is dried to produce non-hydrated {(mono-trichloro,) tetra-(monopotassium dichloro,)} penta-isocyanurate.

5. A process for preparing non-hydrated {(mono-trichloro,) tetra-(monopotasium dichloro,)} penta-isocyanurate, which comprises bringing together under pressure and reacting in a substantially dry state potassium dichloroisocyanurate monohydrate and non-hydrated dichloroisocyanuric acid, in amounts such that the molar ratio of said acid is in the range of 1:1 to 3:1.

6. Process of claim 5 wherein the potassium dichloroisocyanurate monohydrate and the non-hydrated dichloroisocyanuric acid are brought together under pressure and reacted by blending said reactants and by compacting the blended product under a pressure of from about 1,000 psig to about 20,000 psig.

7. A process for preparing non-hydrated {(mono-trichloro,) tetra-(monopotassium) dichloro,)} penta-isocyanurate which comprises bringing together and reacting in a substantially dry state potassium dichloroisocyanurate monohydrate and dichloroisocyanuric acid monohydrate by blending said reactants in amounts such that the molar ratio of the potassium dichloroisocyanurate monohydrate to said acid is in the range of 1:1 to 3:1, and compacting the blended reaction product under a pressure of from about 1,000 psig to about 20,000 psig to remove hydrate water.

8. A process for preparing non-hydrated {(mono-trichloro,) tetra-(monopotassium dichloro,)} penta-isocyanurate which comprises bringing together and reacting in a substantially dry state potassium dichloroisocyanurate monohydrate and dichloroisocyanuric acid monohydrate by blending said reactants in amounts such that the molar ratio of the potassium dichloroisocyanurate monohydrate to said acid is in the range of 1:1 to 3:1, and drying the blended reaction product to remove hydrate water.

* * * * *